United States Patent [19]

Van Peppen

[11] Patent Number: 5,015,787

[45] Date of Patent: May 14, 1991

[54] PROCESS FOR PRODUCTION CYCLOHEXANOL

[75] Inventor: Jan F. Van Peppen, Chester, Va.

[73] Assignee: Allied-Signal Inc., Morris Township, Morris County, N.J.

[21] Appl. No.: 335,337

[22] Filed: Apr. 10, 1989

[51] Int. Cl.$^5$ .................. C07C 29/20; C07C 35/08
[52] U.S. Cl. .................. 568/835; 568/814; 568/830
[58] Field of Search .................. 568/814, 810, 835

[56] References Cited

U.S. PATENT DOCUMENTS

| | | | |
|---|---|---|---|
| 2,794,056 | 5/1957 | Winstrom | 568/835 |
| 4,088,703 | 5/1978 | Yeh et al. | 568/835 |
| 4,187,152 | 2/1980 | Roth, Jr. et al. | 568/835 |
| 4,272,326 | 6/1981 | Hertzog et al. | 568/835 |
| 4,664,755 | 5/1987 | Nienhaus et al. | 568/835 |

*Primary Examiner*—Werren B. Lone

[57] ABSTRACT

In a process for production of cyclohexanol comprising the selective catalytic hydrogenation of phenol to a product mixture comprising a major portion of cyclohexanol and a substantially smaller portion of cyclohexanone, then distillation of said product mixture to obtain cyclohexanol containing a minor amount of cyclohexanone meeting desired specification levels; the improvement comprising adding to said product mixture an effective amount of a polyamine such as hexamethylene diamine and distilling the product mixture to obtain an improved yield of said cyclohexanol containing a minor amount of cyclohexanone.

12 Claims, No Drawings

PROCESS FOR PRODUCTION CYCLOHEXANOL

BACKGROUND OF THE INVENTION

1. Field of the Invention

This invention relates to the production of cyclohexanol by the catalytic hydrogenation of phenol.

2. Description of the Prior Art

The manufacture of cyclohexanol by catalytic hydrogenation of phenol is known, as shown in U.S. Pat. No. 3,998,884 to Gibson, issue date Dec. 21, 1976, and U.S. Pat. No. 2,794,056 to Winstrom, issue date May 28, 1957. Phenol is subjected to catalytic hydrogenation under conditions known in the art which effect conversion of phenol substantially to cyclohexanol. Cyclohexanone is a byproduct in this process, which must be removed by distillation to meet product specifications in the merchant market. The more cyclohexanone to be removed, the higher the energy costs and the smaller the yield of cyclohexanol meeting required product specifications. In a typical batch process, during the final stages of phenol conversion to cyclohexanol, the amount of cyclohexanone produced may rise to 0.2 to 0.3 weight percent, a level that is in excess of most commercial product specifications that provide for a maximum level of cyclohexanone in cyclohexanol.

The need exists to provide an efficient process to increase the yield of cyclohexanol meeting required product specifications regarding the maximum levels of cyclohexanone permitted.

SUMMARY OF THE INVENTION

In a process for production of cyclohexanol comprising the selective catalytic hydrogenation of phenol to a product mixture comprising a major portion of cyclohexanol and a substantially smaller portion of cyclohexanone, then distillation of said product mixture to obtain cyclohexanol containing a minor amount of cyclohexanone meeting desired specification levels;

the improvement comprising adding to said product mixture an effective amount of a compound selected from the group consisting of (a) a polyamine of the formula

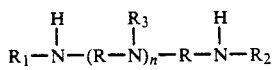

wherein n is an integer from 0 to 4; $R_1$, $R_2$ and $R_3$ are independently selected from the group consisting of hydrogen, alkyl, aryl, cycloalkyl, aralkyl and alkaryl; and R independently at each occurrence is selected from the group of radicals consisting of alkylene, arylene, alkylenearylene, dialkylene, cycloalkylene, dialkylene cycloalkylene, and nitrogen containing heterocyclic groups of 5 to 6 carbon atoms;

(b) a polyamine of the formula

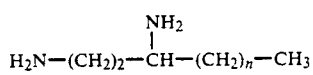

wherein n is 16 or 18;

(c) a polyamine of the formula

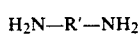

wherein R' is an aliphatic hydrocarbon chain of 36 carbon atoms;

and (d) a polyethylenimine having a molecular weight of about 1,000 to 100,000;

and distilling the product mixture to obtain an improved yield of said cyclohexanol containing a minor amount of cyclohexanone.

DESCRIPTION OF THE PREFERRED EMBODIMENT

The preferred embodiment incorporates a batch-type process for the production of cyclohexanol by the catalytic hydrogenation of phenol to a product mixture comprising a major portion of cyclohexanol, e.g. at least 99 weight percent, and a substantially smaller portion of cyclohexanone as a byproduct, e.g. up to 1 weight percent. Additionally the product mixture will contain smaller amounts of unreacted phenol and other heavy boiling impurities.

A preferred source of phenol is the crude phenol obtained from the decomposition of cumene hydroperoxide. It is not necessary to treat this phenol to reduce its acetol content, as taught by U.S. Pat. No. 3,965,187 to Little et al. issue date June 22, 1976, which teaches the selective hydrogenation of phenol to produce cyclohexanone. Instead, the crude phenol may be directly submitted to the catalytic hydrogenation process step.

In the present invention, a catalyst is chosen which is selective for hydrogenating phenol directly to cyclohexanol. Suitable conditions include use of active hydrogenation catalyst in supported or unsupported form, typical active catalyst ingredients being platinum, Raney nickel, copper, and molybdenum oxide, at temperatures and pressures suitable for use with the particular catalyst, known to those skilled in the art. Raney nickel is a preferred catalyst.

The crude phenol obtained from the decomposition of cumene hydroperoxide is hydrogenated in contact with Raney nickel catalyst to a product mixture comprising a major portion of cyclohexanol and a substantially smaller portion of cyclohexanone.

It is necessary to distill this resulting product mixture to obtain commercial grade cyclohexanol meeting product standards, which may specify a maximum level of cyclohexanone of 0.1 weight percent or less. It is difficult to separate cyclohexanone from cyclohexanol and this is achieved in a commercial process through codistillation utilizing two distillation columns. The product mixture is charged to a first column where cyclohexanone is removed overhead with cyclohexanol. When the bottoms reach a desired level, e.g. about 0.1 weight percent cyclohexanone, the bottoms are transferred to a second distillation column. There the cyclohexanol is distilled overhead containing e.g. less than about 0.1 weight percent cyclohexanone. It can readily be seen that important quantities of cyclohexanol can be lost overhead in the first column, impacting negatively on the yield.

The improvement of this invention comprises adding to the product mixture an effective amount of a compound selected from the group consisting of (a) a polyamine of the formula

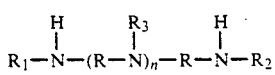

wherein n is an integer from 0 to 4; $R_1$, $R_2$ and $R_3$ are independently selected from the group consisting of hydrogen, alkyl, aryl, cycloalkyl, aralkyl and alkaryl; and R independently at each occurrence is selected from the group of radicals consisting of alkylene, arylene, alkylenearylene, dialkylene, cycloalkylene, dialkylene cycloalkylene, and nitrogen containing heterocyclic groups of 5 to 6 carbon atoms;

(b) a polyamine of the formula

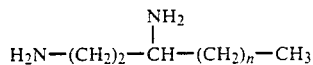

wherein n is 16 or 18;

(c) a polyamine of the formula

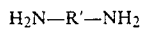

wherein R' is an aliphatic hydrocarbon chain of 36 carbon atoms;

and (d) a polyethylenimine having a molecular weight of about 1,000 to 100,000.

Addition of the compound to the product mixture is conveniently accomplished after removal of the catalyst from the product mixture to avoid any of the added compound from being recycled backward in the process with the catalyst.

A preferred compound is the polyamine (a) wherein $R_1$, $R_2$ and $R_3$ are independently selected from the group of radicals consisting of hydrogen, alkyl of 1–10 carbon atoms, aryl of 6–10 carbon atoms, cycloalkyl of 4–10 carbon atoms, and aralkyl of 7–20 carbon atoms; and R independently at each occurrence is selected from the group consisting of alkylene of 1–40 carbon atoms, arylene of 6–10 carbon atoms, alkylenearylene of 7–20 carbon atoms, dialkylene arylene of 7–20 carbon atoms, cycloalkylene of 4–10 carbon atoms, dialkylene cycloalkylene of 6–20 carbon atoms, and nitrogen containing heterocyclic groups of 5–6 carbon atoms.

Particularly preferred for the polyamine (a) is wherein n is 0 to 1; $R_1$, $R_2$ and $R_3$ are each hydrogen and R is alkylene or arylene.

The polyamines of (a) are meant to include lower alkyl, hydroxy or carboxyl substituted derivatives thereof. The alkyl and alkylene groups in these polyamine compounds may be straight-chain, branched-chain or cyclic. These polyamines may be used in the form of a single compound, as a mixture of isomers, or as a mixture of polyamines containing from 2 to 6 amino nitrogen atoms in the molecule. Additionally the amines may be used in aqueous media containing up to 75% water. Illustrative of suitable polyamines are: ortho, meta and para-xylylene diamine; ortho, meta and para-toluylene diamine; hexamethylene diamine; ortho, meta and para-phenylene diamine; 4,5-diaminoxylene; 3,5-diaminobenzoic acid; 3,4-diaminobenzoic acid; 2,6-diaminopyridine; 1,5-diaminonaphthalene; 1,2-diaminonaphthalene; 1,5-diaminopentane; 1,4-cyclohexanebis (methylamine); N-(3-aminopropyl) cyclohexylamine; N-phenylethylene diamine; 1,3-diamino-2-hydroxypropane; diethylene triamine; di-n-propylene triamine; di-i-butylene triamine; di-n-hexylene triamine; triethylene tetramine; tri-i-propylene tetramine; tri-n-hexylene tetramine; 4-(2-aminoethyl)-diethylene triamine; tetraethylene pentamine; tetra-n-propylene pentamine, tetra-n-butylene pentamine, and pentaethylene hexamine.

The polyethylenimine of (d) is disclosed in U.S. Pat. No. 4,092,360 to Van Peppen et al., incorporated herein by reference.

The amount of compound added is an effective amount relative to the level of cyclohexanone present in the product mixture. An effective amount serves to react with and tie up most of the cyclohexanone into a nonvolatile species. An example of an effective amount would include 0.25 to 10, preferably 1–3 molar equivalents of the polyamine to 1 mole of the cyclohexanone present in the product mixture, though greater or lesser amounts could be chosen, with resulting varying degrees of effectiveness. Given the teachings herein one skilled in the art can select an amount of the polyamine to achieve desired separation of cyclohexanone and improved yield of cyclohexanol.

EXAMPLE 1

A crude cyclohexanol (OL) sample was treated with hexamethylene diamine (HMDA) in the following manner. The crude OL contained 0.80 weight percent cyclohexanone (ONE) and 0.03 weight percent phenol. In each experiment, 100 g crude OL (0.082 mole ONE) was transferred to a 500 ml 3 necked flask provided with a thermometer, magnetic stirring bar, and nitrogen blanket. The reaction of ONE and HMDA were carried out at 130° C. and 160° C. The 100 g crude OL was raised to the desired temperature, then 0.57 g (0.0098 molar eq.) HMDA were added. Periodically a 1 gram sample was withdrawn for analysis. The results of the analysis are given below.

| | Time, min. | ONE, wt. % | Phenol, wt. % |
|---|---|---|---|
| 130° C. | | | |
| | 30 | 0.35 | 0.02 |
| | 60 | 0.41 | 0.03 |
| | 120 | 0.40 | N.D. |
| 160° C. | | | |
| | 30 | 0.38 | N.D. |
| | 60 | 0.40 | N.D. |
| | 90 | 0.37 | N.D. |

The above experiments clearly show that ONE was not consumed or irreversably bound by HMDA under these prevailing reaction conditions.

The reaction mixture from the last experiment at 160° C. was subjected to flash distillation. The distillate was found to contain 0.02 weight percent ONE and below detectable (N.D.) limits of phenol. Thus, in the procedure of distillation the ONE became more securely bound to the HMDA.

EXAMPLE 2

In this example, crude OL was again treated with HMDA, this time in conjunction with distillation. In the plant process distillation the bottoms typically are at about 100° to 120° C. These temperatures were matched by conducting the distillation under reduced pressure. To minimize the effects of water or other lights, about 10% of the charge was distilled over before HMDA was added. In each experiment below, 330 grams of crude OL was charged to a 500 ml flask equipped with a septum arrangement, a short-path distillation head and downward condenser, a thermometer, a magnetic stirring bar and provided with vacuum. The contents of the flask were heated under vacuum to remove 30 grams of "lights" overhead. Then 0.63 ml (0.0091 molar eq.) HMDA were added to the remaining 300 g of crude OL containing 0.15 weight percent (0.045 mole) ONE. The amount of HMDA was equivalent to 1.76 lbs. per 1000 lbs. crude OL. Distillation was continued, reaction time was begun from this moment. Successive overhead cuts were collected for ONE assay.

| Overhead, % (of 300 g batch) | ONE, wt. % |
|---|---|
| Experiment at 100° C. Pressure: 80 mm Hg | |
| 0–4 | 0.19 |
| 12–17 | 0.09 |
| 21–26 | 0.06 |
| Experiment at 120° C. Pressure: 170 mm Hg | |
| 0–6 | 0.13 |
| 18–23 | 0.05 |
| 23–32 | 0.03 |

EXAMPLE 3

Control

In the plant process, a batch reactor was charged with 20,000 pounds of phenol. The reactor contained a Raney nickel catalyst. At a temperature of 135° to 150° C. the phenol was hydrogenated to cyclohexanol. At the end of the reaction it was found that approximately 0.25–0.35% of byproduct cyclohexanone was present. The hydrogenation product was separated from the catalyst by decanting and filtering. The catalyst was returned to the batch reactor and again 20,000 pounds of phenol were charged as well as sufficient catalyst to achieve the desired rate of reaction and the hydrogenation was repeated. This procedure of batch operation was carried out continuously.

The product from the batch hydrogenations were distilled on a continuous basis to remove overhead a mixture of cyclohexanone and cyclohexanol. When the bottoms contained approximately 0.1% of cyclohexanone the bottoms were transferred to a second distillation column. In the second distillation column cyclohexanol was distilled overhead. The overheads contained less than approximately 0.1% of cyclohexanone. In this manner, the yield of cyclohexanone from the second distillation column was approximately 900 pounds per hour.

Addition of Hexamethylene Diamine

The product from the batch hydrogenations having the catalyst removed as described above was mixed with HMDA. The amount of HMDA added was approximately 40 pounds per hydrogenation batch (20,000 lbs. of hydrogenation product).

The mixture of hydrogenation product and HMDA was distilled continuously as described above, through the first column to remove a mixture of cyclohexanone and cyclohexanol and then through the second column to obtain cyclohexanol containing less than 0.1% of cyclohexanone. In this manner, the yield of cyclohexanol was approximately 1,200 pounds per hour.

EXAMPLE 4

HMDA was added to crude OL (0.30 wt. % ONE) from a batch hydrogenation after the nickel catalyst was removed and before feeding to the distillation column, the procedure according to Example 3, then submitted to flash distillation. With 2 lbs. HMDA/1000 lbs. crude OL (ratio of molar equivalents, NH$_2$/C=O=1.1) the distillate contained 0.04 weight percent ONE. With 1 lb. HMDA/1000 lbs. crude OL (ratio of molar equivalents, NH$_2$/C=O=0.55) the distillate contained 0.08 weight percent ONE. A similar procedure without the addition of HMDA resulted in distillate containing 0.24 weight percent ONE.

What is claimed:

1. In a process for production of cyclohexanol comprising the selective catalytic hydrogenation of phenol to a product mixture comprising a major portion of cyclohexanol and a substantially smaller portion of cyclohexanone, then distillation of said product mixture to obtain cyclohexanol containing a minor amount of cyclohexanone meeting desired specification levels;

the improvement comprising adding to said product mixture an effective amount of a compound selected from the group consisting of (a) a polyamine of the formula

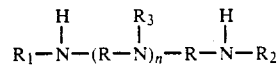

wherein n is an integer from 0 to 4; $R_1$, $R_2$ and $R_3$ are independently selected from the group consisting of hydrogen, alkyl, aryl, cycloalkyl, aralkyl and alkaryl; and R independently at each occurrence is selected from the group of radicals consisting of alkylene, arylene, alkylenearylene, dialkylene, cycloalkylene, dialkylene cycloalkylene, and nitrogen containing heterocyclic groups of 5 to 6 carbon atoms;

(b) a polyamine of the formula

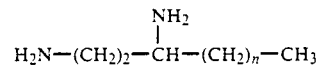

wherein n is 16 or 18;

(c) a polyamine of the formula

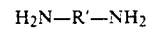

wherein R' is an aliphatic hydrocarbon chain of 36 carbon atoms;

and (d) a polyethylenimine having a molecular weight of about 1,000 to 100,000;

and distilling the product mixture to obtain an improved yield of said cyclohexanol containing a minor amount of cyclohexanone.

2. The process of claim 1 wherein said compound is added to said product mixture in an amount of 0.25 to 10 molar equivalents of compound to 1 mole of cyclohexanone present in the product mixture.

3. The process of claim 2 wherein said amount of compound added is 1 to 3 molar equivalents to 1 mole of cyclohexanone.

4. The process of claim 1 wherein said compound added to said product mixture is (a), wherein $R_1$, $R_2$ and $R_3$ are independently selected from the group of radicals consisting of hydrogen, alkyl of 1–10 carbon atoms, aryl of 6–10 carbon atoms, cycloalkyl of 4–10 carbon atoms, and aralkyl of 7–20 carbon atoms; and R independently at each occurrence is selected from the group consisting of alkylene of 1–40 carbon atoms, arylene of 6–10 carbon atoms, alkylenearylene of 7–20 carbon atoms, dialkylene arylene of 7–20 carbon atoms, cycloalkylene of 4–10 carbon atoms, dialkylene cycloalkylene of 6–20 carbon atoms, and nitrogen containing heterocyclic groups of 5–6 carbon atoms.

5. The process of claim 4 wherein for (a), n is 0 to 1; $R_1$, $R_2$, and $R_3$ are each hydrogen and R is alkylene or arylene.

6. The process of claim 5 wherein said compound is added to said product mixture in an amount of 0.25 to 10 molar equivalents of compound to 1 mole of cyclohexanone present in the product mixture.

7. The process of claim 6 wherein said amount of compound added is 1 to 3 molar equivalents to 1 mole of cyclohexanone.

8. The process of claim 1 wherein said compound added to said product mixture is hexamethylene diamine.

9. The process of claim 8 wherein said compound is added to said product mixture in an amount of 0.25 to 10 molar equivalents of compound to 1 mole of cyclohexanone present in the product mixture.

10. The process of claim 9 wherein said amount of compound added is 1 to 3 molar equivalents to 1 mole of cyclohexanone.

11. The process of claim 1 wherein said compound added to said product mixture is (d) in an amount of 0.25 to 10 molar equivalents of compound to 1 mole of cyclohexanone present in the product mixture.

12. The process of claim 11 wherein said amount of compound added is 1 to 3 molar equivalents to 1 mole of cyclohexanone.

* * * * *